United States Patent [19]

Kisida et al.

[11] Patent Number: 4,474,796
[45] Date of Patent: Oct. 2, 1984

[54] INSECTICIDAL SUBSTITUTED HYDANTOINS

[75] Inventors: Hirosi Kisida, Takarazuka; Makoto Hatakoshi, Minoo, both of Japan

[73] Assignee: Sumitomo Chemical Company, Limited, Osaka, Japan

[21] Appl. No.: 463,545

[22] Filed: Feb. 4, 1983

[51] Int. Cl.$^3$ .................... A01N 43/50; C07D 233/82
[52] U.S. Cl. ............................... 424/273 R; 548/311; 548/312
[58] Field of Search ..................... 548/311; 424/273 R

[56] References Cited

FOREIGN PATENT DOCUMENTS 353544  5/1976  U.S.S.R. ............................ 548/311

OTHER PUBLICATIONS

Ware, E., *Chem. Rev.*, 46, p. 434, (1950).

*Primary Examiner*—Richard A. Schwartz
*Attorney, Agent, or Firm*—Stevens, Davis, Miller & Mosher

[57] ABSTRACT

A compound of the formula,

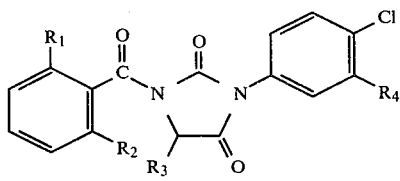

wherein $R_1$ is a halogen atom or methyl group, $R_2$ is hydrogen or a halogen atom, $R_3$ is chlorine or bromine atom and $R_4$ is hydrogen or chlorine atom, which is useful as an insecticide.

8 Claims, No Drawings

INSECTICIDAL SUBSTITUTED HYDANTOINS

The present invention relates to a substituted hydantoin of the formula,

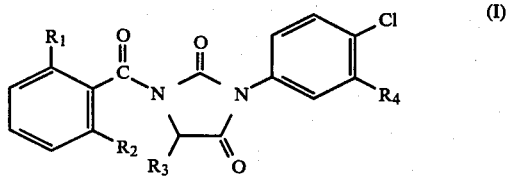

wherein $R_1$ is a halogen atom (preferably fluorine or chlorine atom) or methyl group, $R_2$ is hydrogen or a halogen atom (preferably fluorine or chlorine atom), $R_3$ is chlorine or bromine atom, $R_4$ is hydrogen or chlorine atom; a process for producing it; and an insecticidal composition containing it. Compounds of the present invention possess useful insecticidal activities and can be obtained by e.g. the following production process. Namely, a compound of the formula,

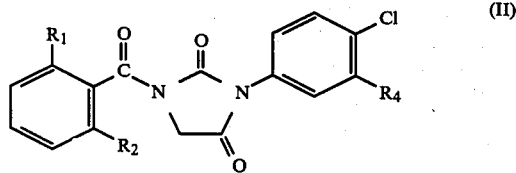

wherein $R_1$, $R_2$ and $R_4$ are each as defined above, is reacted with chlorine or bromine, the amount of which is preferably more than 1 equivalent, in the presence of organic solvent such as lower alkanoic acid at a temperatures of 0° C. to 250° C. for a period of 1 to 50 hours. The crude product is purified, if necessary, by chromatography or recrystallization.

The compound (II) may be prepared by per se conventional procedures, of which typical examples are as follows:

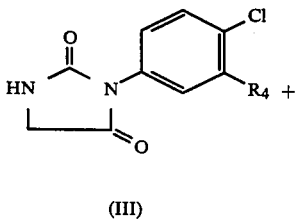

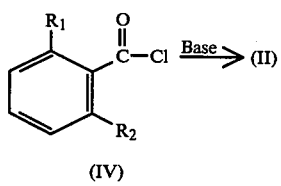

wherein $R_1$, $R_2$ and $R_4$ are each as defined above. A method for the preparation of the substituted hydantoins of the present invention will be illustrated in more detail with reference to the following examples.

EXAMPLE 1

3-(4-Chlorophenyl)-1-(2,6-difluorobenzoyl)hydantoin (1.50 g; 4.3 mmol) was dissolved in acetic acid (50 ml). The solution was heated to reflux and bromine (2.06 g; 13 mmol) was added dropwise over a five-hour interval. The reaction mixture was heated under reflux for further two hours and the solvent was evaporated off under reduced pressure. After adding water, the product was extracted with methylene chloride (50 ml). The solution was washed with water, a saturated sodium bicarbonate solution and water. The solvent was removed by evaporation and the oily residue was purified on a column packed with 50 grams of silica gel by using methylene chloride as eluent. 0.95 Grams (yield: 51.4%) of the objective compound, 5-bromo-3-(4-chlorophenyl)-1-(2,6-difluorobenzoyl)hydantoin, was obtained as white crystals melting at 185°–186° C.

|     | Elementary analysis | | | | |
| --- | --- | --- | --- | --- | --- |
|     | C (%) | H (%) | N (%) | Br (%) | Cl (%) |
| (C) | 44.73 | 1.88 | 6.52 | 18.60 | 8.25 |
| (F) | 45.13 | 1.76 | 6.38 | 18.55 | 7.94 |

EXAMPLE 2

Instead of bromine in Example 1, Example 2 was performed using chlorine gas which was bubbled into the solution in a ratio of 10 ml/min for 5 hours. After the similar work-up, 1.27 grams (yield: 76.5%) of the objective compound, 5-chloro-3-(4-chlorophenyl)-1-(2,6-difluorobenzoyl)hydantoin, was obtained as white crystals melting at 187°–188° C.

In the following Table 1, the compounds obtained as described above were shown. The compound number described here are common in the following formulation examples and test examples.

TABLE 1

| Compound No. | $R_1$ | $R_2$ | $R_3$ | $R_4$ | Physical constant |
| --- | --- | --- | --- | --- | --- |
| 1  | F   | F  | Br | H  | M.P. 185–186° C. |
| 2  | F   | F  | Br | Cl | $n_D^{22.0}$ 1.5852 |
| 3  | Cl  | H  | Br | H  | M.P. 160–161° C. |
| 4  | CH3 | H  | Br | H  | $n_D^{25.0}$ 1.5974 |
| 5  | Cl  | Cl | Br | H  | M.P. 50–51° C. |
| 6  | F   | F  | Cl | H  | M.P. 187–188° C. |
| 7  | F   | F  | Cl | Cl | $n_D^{24.0}$ 1.5865 |
| 8  | Cl  | H  | Cl | H  | $n_D^{27.0}$ 1.5922 |
| 9  | CH3 | H  | Cl | H  | $n_D^{26.5}$ 1.5981 |
| 10 | Cl  | Cl | Cl | H  | $n_D^{27.0}$ 1.5915 |

On the practical application as insecticides the compounds (I) are used in the form of an appropriate composition such as emulsifiable concentrates, dusts, granules, wettable powders and fine granules and the content of the compound (I) in such composition may be from about 0.1 to 99% by weight, preferably from about 2.0 to 80.0% by weight.

The composition can be formulated in a per se conventional manner by mixing at least one of the compounds (I) with an appropriate solid or liquid carrier(s) or diluent(s) with or without an appropriate adjuvant(s) (e.g. surfactants, adherents, dispersants, stabilizers) for improving the dispersibility and other properties of the active ingredient on use.

Examples of the solid carriers or diluents are clays (e.g. kaolin, bentonite, fuller's earth, pyrophyllite, sericite), talcs, other inorganic materials (e.g. hydrated silica, pumice, diatomaceous earth, sulfur powder, active carbon) in fine powders or powdery form.

Examples of the liquid carriers or diluents are alcohols (e.g. methanol, ethanol), ketones (e.g. acetone, methyl ethyl ketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. kerosene, lamp oil), esters, nitriles, acid amides (e.g. dimethylformamide, dimethylacetamide), halogenated hydrocarbons (e.g. dichloroethane, trichloroethylene, carbon tetrachloride), etc.

Examples of the surfactants are alkylsulfates, alkylsulfonates, alkylarylsulfonates, polyethylene glycol ethers, polyhydric alcohol esters, etc. Examples of the adherents and dispersants may include casein, gelatin, starch powder, carboxymethyl cellulose, gum arabic, alginic acid, ligninsulfonate, bentonite, molasses, polyvinyl alcohol, pine oil and agar. As the stabilizers, there may be used PAP (isopropyl acid phosphates mixture), TCP (tricresyl phosphate), tolu oil, epoxydized oil, various surfactants, various fatty acids and their esters, etc.

In addition, the said composition may contain insecticides, insect control agents, acaricides, nematicides, fungicides, herbicides, plant growth regulators, fertilizers, soil improvers, etc. Particularly when employed in conjunction with conventional insecticides, a broad spectrum of activity or a more immediate effect on very heterogeneous populations is provided. Examples of the insecticides include organic phosphorus compounds (e.g. fenitrothion (O,O-dimethyl-O-(3-methyl-4-nitrophenyl)phosphorothioate), malathion (S-[1,2-bis(ethoxycarbonyl)ethyl]O,O-dimethylphosphorothioate), dimethoate (O,O-dimethyl-S-(N-methylcarbamoylmethyl)phosphorodithioate), salithion (2-methoxy-4H-1,3,2-benz-dioxaphosphorin-2-sulfide), diazinon (O,O-diethyl-O-(2-isopropyl-6-methyl-4-pyrimydinyl)phosphorothioate), dipterex (2,2,2-trichloro-1-hydroxyethyl-O,O-dimethylphosphonate), dichlorvos (O-(2,2-dichlorovinyl)-O,O-dimethylphosphate), etc.), carbamate compounds (e.g. MPMC (3,4-dimethylphenyl-N-methylcarbamate), MTMC (m-tolyl N-methylcarbamate), BPMC (2-sec-butylphenyl N-methylcarbamate), carbaryl (1-naphthyl N-methylcarbamate), etc.) and pyrethroid compounds (e.g. permethrin (3-phenoxybenzyl-d,l-cis,trans-3-(2,2-dichlorovinyl)-2,2-dimethylcyclopropanecarboxylate), fenvalerate (α-cyano-m-phenoxybenzyl α-isopropyl-p-chlorophenylacetate, etc.).

The compounds (I) of the invention formulated into an appropriate composition may be applied in a suitable application method such as spraying, smoking or soil treatment.

Some practical embodiments of the composition for the control of insects according to the invention are illustratively shown in the following Formulation Examples wherein % and part(s) are by weight.

FORMULATION EXAMPLE 1

Each of Compound Nos. 1 to 10 (20 parts), an emulsifier (a mixture of polyoxyethylene-styrenated phenyl ether, polyoxyethylene-styrenated phenyl ether polymer and an alkylarylsulfonate) (20 parts) and xylene (60 parts) are mixed well to make an emulsifiable concentrate containing the active ingredient in a concentration of 20%.

FORMULATION EXAMPLE 2

Each of Compound Nos. 1 to 10 (20 parts) and an emulsifier (sodium laurylsulfate) (5 parts) are mixed well, and diatomaceous earth (300 mesh) (75 parts) is added thereto, and the resultant mixture is mixed well in a pulverizer to make a wettable powder containing the active ingredient in a concentration of 20%.

FORMULATION EXAMPLE 3

Each of Compound Nos. 1 to 10 (3 parts) is dissolved in acetone (20 parts), talc (300 mesh) (97 parts) is added thereto, and the resultant mixture is mixed well in a pulverizer. Then, acetone is eliminated by evaporation to give a dust containing the active ingredient in a concentration of 3%.

FORMULATION EXAMPLE 4

Each of Compound Nos. 1 to 10 (5 parts), a dispersant (calcium ligninsulfonate) (2 parts) and kaolin (93 parts) are mixed well in a pulverizer. To the resultant mixture, water is added in an amount of 10%, and the resulting mixture is kneaded well and granulated by the aid of a granulator, followed by drying to give granules containing the active ingredient in a concentration of 5%.

FORMULATION EXAMPLE 5

Each of Compound Nos. 1 to 10 (2 parts), a dispersant (calcium lingninsulfonate) (2 parts) and clay (96 parts) are mixed well in a pulverizer. Water is added to the resultant mixture in an amount of 10%. The resulting mixture is mixed well and granulated by the aid of a granulator. The granules are dried to give fine granules containing the active ingredient in a concentration of 2%.

The following Examples show some typical test data indicating the excellent insecticidal activity of the compounds (I). The compound used for comparison is as follows:

| Compound No. | Chemical structure | Remarks |
|---|---|---|
| A | (CH$_3$O)$_2$P(=S)—O—⟨phenyl(CH$_3$)⟩—SCH$_3$ | Commercially available insecticide "fenthion" |

TEST EXAMPLE 1

An emulsifiable concentrate prepared in the same manner as in Formulation Example 1 was diluted with water to make a 400 fold dilution. Two ml of the solution were applied to the artificial diet (15 g) for tobacco cutworms placed in a polyethylene cup of 11 cm in diameter. Ten third-instar larvae of tobacco cutworms (Spodoptera litura) were released into the cup and the number of the dead and the alive insects was observed after 6 days to calculate the mortality (4 replications). The results are shown in Table 2.

TABLE 2

| Compound No. | Mortality (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| Untreated | 0 |

TEST EXAMPLE 2

The $LC_{50}$ value against the third-inster larvae of tobacco cutworms (*Spodoptera litura*) was determined in the same manner as in Test Example 1. The results are shown in Table 3.

TABLE 3

| Compound No. | $LC_{50}$ (ppm) |
|---|---|
| 1 | 32 |
| 2 | 27 |
| 3 | 52 |
| 4 | 56 |
| 6 | 27 |
| 7 | 25 |
| 8 | 48 |
| 9 | 55 |
| A | 320 |

TEST EXAMPLE 3

A wettable powder prepared according to Formulation Example 2 was diluted with water to make a 400 fold dilution. The solution (0.7 ml) was added to 100 ml of distilled water. The last instar larvae of common mosquitoes (*Culex pipiens pallens*) were released therein. The diet was put and the larvae were reared until their emergence. The rate of emergence was observed (2 replications). The results are shown in Table 4.

TABLE 4

| Compound No. | Concentration (ppm) | Rate of emergence (%) |
|---|---|---|
| 1 | 3.5 | 0 |
| 2 | 3.5 | 0 |
| 5 | 3.5 | 0 |
| 6 | 3.5 | 0 |
| 7 | 3.5 | 0 |
| 10 | 3.5 | 0 |
| Untreated | — | 92.5 |

TEST EXAMPLE 4

An emulsifiable concentrate prepared in the same manner as in Formulation Example 1 was diluted with water to make a 400 fold dilution. An artificial diet (5 g) for rice stem borer in a polyethylene cup of 5.5 cm in diameter was wet with 0.7 ml of the diluted sample (500 ppm in concentration). After air dried, ten 10-day old larvae of rice stem borers (*Chilo suppressalis*) were released into the cup and the number of the dead and the alive insects was observed after 8 days. As the results, all compounds showed the mortality over 80%.

What is claimed is:

1. A compound of the formula

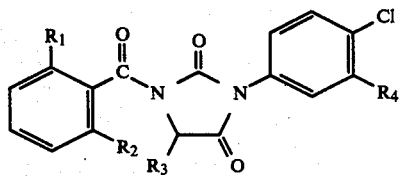

wherein $R_1$ is a halogen atom or methyl group, $R_2$ is hydrogen or a halogen atom, $R_3$ is chlorine or bromine atom and $R_4$ is hydrogen or chlorine atom.

2. The compound according to claim 1, wherein $R_1$ and $R_2$ are each fluorine atom or chlorine atom, $R_3$ is chlorine or bromine atom and $R_4$ is hydrogen atom.

3. The compound according to claim 1, which has the formula,

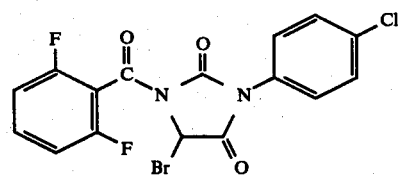

4. The compound according to claim 1, which has the formula,

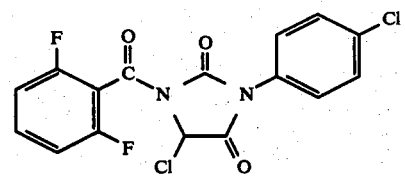

5. The compound according to claim 1, which has the formula,

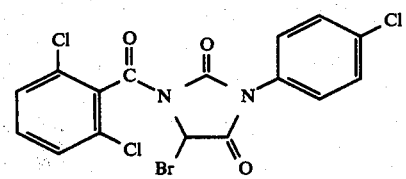

6. An insecticidal composition containing an inert carrier and as an active ingredient an insecticidally effective amount of the compound according to claim 1.

7. The insecticidal composition according to claim 6, wherein the content of the active ingredient is from 0.1 to 99% by weight.

8. A method for controlling insects which comprises applying an insecticidally effective amount of the compound according to claim 1 to said insects.

* * * * *